United States Patent [19]

Raabe et al.

[11] 4,216,314

[45] Aug. 5, 1980

[54] N-ARYLOXYPROPYL-N'-DIOXOPYRIMI-DYL-α,ω-ALKYLENEDIAMINES

[75] Inventors: Thomas Raabe, Rodenbach; Otto Gräwinger, Frankfurt am Main; Josef Scholtholt, Hanau; Eckhard Schraven, Frankfurt am Main, all of Fed. Rep. of Germany

[73] Assignee: Cassella Farbwerke Mainkur Aktiengesellschaft, Frankfurt, Fed. Rep. of Germany

[21] Appl. No.: 902,000

[22] Filed: May 2, 1978

[30] Foreign Application Priority Data

May 16, 1977 [LU] Luxembourg .............................. 77339

[51] Int. Cl.$^2$ .................... C07D 413/12; C07D 239/54
[52] U.S. Cl. ..................................... 544/123; 544/310; 544/312; 424/248.54; 424/251
[58] Field of Search ....................... 544/123, 312, 310; 424/248.54, 251

[56] References Cited

U.S. PATENT DOCUMENTS

| 3,852,291 | 12/1974 | Augstein et al. ..................... 544/312 |
| 4,020,071 | 4/1977 | Raabe et al. .......................... 424/251 |

*Primary Examiner*—Henry R. Jiles
*Assistant Examiner*—R. W. Ramsuer
*Attorney, Agent, or Firm*—Berman, Aisenberg & Platt

[57] ABSTRACT

Physiologically-acceptable substituted 1,2-ethylenediamines and 1,3-propylenediamines, in free-base and in acid-addition-salt form, have highly pronounced and cardioselective β-adrenolytic action, antiarrhythmic action and hypotensive action on administration to humans. The diamines are, more specifically, N-[3-aryloxy-2-hydroxypropyl]-N'-[1,3-(di-R$^3$)-2,4-dioxypyrimid-6-yl] (ethylene or propylene)diamines wherein R$^3$ is —H or lower alkyl and the aryl nucleus is either further unsubstituted, further monosubstituted or further disubstituted.

The compounds are prepared, e.g, by reacting a corresponding N-[3-phenoxy-2-hydroxypropyl] (ethylene or propylene)diamine with a corresponding 6-chloropyrimidine-2,4-dione in a suitable medium containing an acid-binding agent.

Such compounds are administered orally or parenterally in effective, but substantially non-toxic, doses either in substantially pure form, in virtually any standard dosage form or in combination with one or more other pharmacologically- and chemically-compatible drugs.

34 Claims, No Drawings

N-ARYLOXYPROPYL-N'-DIOXOPYRIMIDYL-α,ω-ALKYLENEDIAMINES

SUMMARY

N-[3-(unsubstituted, monosubstituted or disubstituted aryloxy-2-hydroxypropyl]-N'-[(unsubstituted or 1,3-di{lower}alkyl)-2,4-dioxopyrimid-6-yl]-α,ω-(ethylene or n-propylene)diamines are physiologically active. Pharmacologically-acceptable embodiments, in free-base or in acid-addition-salt form, are useful for treating or for prophylaxis of heart complaints and heart diseases, such as angina pectoris and cardiac arrhythmias. They are also useful for reducing blood pressure and have virtually no adverse side effects on lungs of even sensitive patients. The unsubstituted, monosubstituted or disubstituted aryloxy is, e.g., optionally-substituted phenoxy with at most 2 ring substituents which are independently selected from the group consisting of hydroxyl; halo; nitro; trifluoromethyl; hydrocarbyl having up to 8 carbon atoms; hydrocarbyloxy having up to 8 carbon atoms; alkanoyl having from 1 to 6 carbon atoms; alkoxyalkoxy having up to 8 carbon atoms; alkoxyalkyl having from 2 to 6 carbon atoms; hydroxyalkoxy having from 2 to 6 carbon atoms; hydrocarbylcarbonylamino having up to 12 carbon atoms; ureido; ureido monosubstituted in the 3-position by a substituent selected from the group consisting of alkyl with from 1 to 6 carbon atoms, alkenyl with from 3 to 6 carbon atoms and cycloalkyl with 5 or 6 ring carbon atoms; 3,3-disubstituted ureido, each substituent of which is, independently, lower alkyl or lower alkenyl; morpholino-CO-NH; piperidino-CO-NH-; and 1-pyrrolidinyl—CO—NH-.

DETAILS

Alkylenediamine derivatives of the formula

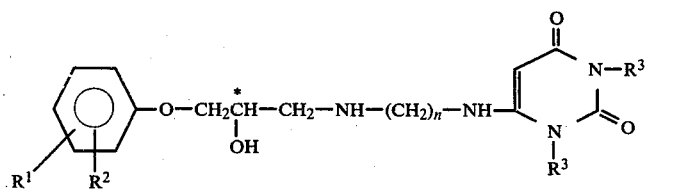

wherein each of

R$^1$ and R$^2$ is, independently, e.g., a hydrogen atom (—H), hydroxyl (—OH), halo, nitro, trifluoromethyl, alkyl, alkenyl, alkinyl, cycloalkyl, cycloalkenyl, alkoxy, cycloalkoxy, alkenyloxy, alkinyloxy, phenalkoxy, alkanoyl, alkoxyalkoxy, alkoxyalkyl, hydroxyalkoxy, phenyl, acrylamino, ureido, substituted ureido, morpholino—CO—NH—, piperidino—CO—NH— or 1-pyrrolidinyl—CO—NH—;

R$^3$ is a hydrogen atom (—H) or lower alkyl; and n is 2 or 3;

and their acid-addition salts are pharmacologically-active compounds. Those which are substantially non-toxic and thus physiologically acceptable are therapeutically useful. Those acid-addition salts which are toxic solely because of the acid from which the acid-addition salt was formed are useful intermediates for the preparation of the corresponding free base or for the preparation of corresponding non-toxic acid-addition salts by conventional methods.

Compounds of formula I have an asymmetric carbon atom in the alkanolamine side chain and thus exist in racemic and in optically-active forms. Compounds of formula I include stereo-isomers, optically-active compounds (enantiomers) and mixtures thereof, particularly racemates, all of which are pharmacologically active.

The physiologically-acceptable compounds, in freebase form as depicted in formula I or in acid-addition-salt form, are administered as such, in combination with one or more other therapeutically- and chemically-compatible drugs or in virtually any known unit dosage form. They are administered orally or parenterally, but oral administration is preferred. They are administered in a single daily dose or in form two to four divided, e.g. after each meal and/or in the evening, doses.

In addition to hydrogen (—H), hydroxyl, trifluoromethyl, nitro and phenyl, the substituents for R$^1$ and R$^2$ have, in particular, the following meanings: alkyl with from 1 to 8, preferably from 1 to 4, carbon atoms, for example methyl, ethyl, propyl, isopropyl, n-butyl, isobutyl, tert.-butyl, sec.-butyl, n-pentyl, isopentyl, neopentyl, tert.-pentyl, n-hexyl, isohexyl, n-heptyl or n-octyl; alkenyl with up to 6 carbon atoms, for example vinyl, allyl, 1-propenyl, isopropenyl, methallyl, crotyl, 2-pentenyl or 2-hexenyl; alkinyl with up to 6 carbon atoms, for example propargyl; cycloalkyl with from 5 to 8 ring carbon atoms, preferably cyclopentyl and cyclohexyl; cycloalkenyl with from 5 to 8 ring carbon atoms and up to two double bonds, preferably cyclopentenyl; alkoxy with from 1 to 8 carbon atoms, for example methoxy, ethoxy, propoxy, butoxy, isopropoxy, isohexyloxy, n-heptyloxy, n-octyloxy or pentyloxy; cycloalkoxy with from 5 to 8 ring carbon atoms, preferably cyclopentyloxy or cyclohexyloxy; alkenyloxy with up to 6 carbon atoms, for example allyloxy, methallyloxy, crotyloxy or 2-hexenyloxy; alkinyloxy with up to 6 carbon atoms, for example propargyloxy; alkanoyl with from 1 to 6 carbon atoms, for example formyl, acetyl, propionyl, butyryl, isobutyryl, valeryl, isovaleryl or pivaloyl; alkoxyalkoxy with a total of up to 8 carbon atoms, wherein the alkoxyalkoxy radical is of the form R$^5$O—R$^4$O— and R$^4$ represents an alkylene radical with from 2 to 7 carbon atoms, R$^5$ represents an alkyl radical with from 1 to 6 carbon atoms and the radicals R$^4$ and/or R$^5$ are optionally branched when they have 3 or more carbon atoms. Examples of suitable alkoxyalkoxy radicals are: 2-methoxyethoxy, 2-ethoxyethoxy, 3-methoxy-n-propoxy, 2-methoxy-n-propoxy, 4-methoxy-n-butoxy, 3-ethoxy-n-propoxy, 2-ethoxy-n-propoxy, 4-ethoxy-n-butoxy, 3-ethoxy-n-butoxy, 2-ethoxy-n-butoxy, 2,2-dimethyl-2-ethoxyethoxy, 3-(n-propoxy)-n-propoxy, 2-(n-propoxy)-n-propoxy, 3-isopropoxy-n-propoxy, 2-isopropoxy-n-propoxy, 2-(n-propoxy)ethoxy, 2-isopropoxyethoxy, 4-(n-propoxy)-n-butoxy, 3-(n-propoxy)-n-butoxy, 2-(n-butoxy)ethoxy, 2-(sec.-butoxy)ethoxy, 2-(tert.-butoxy)ethoxy, 3-(n-butoxy)-n-propoxy, 2-(n-butoxy)-n-propoxy, 3-isobutoxy-n-propoxy, 3-(sec.-butoxy)-n-propoxy, 3-

(tert.-butoxy)-n-propoxy, 4-(n-butoxy)-n-butoxy, 3-(n-butoxy)-n-butoxy, 2-(n-butoxy)-n-butoxy, 4-isobutoxy-n-butoxy, 3-isobutoxy-n-butoxy, 2-(sec.-butoxy)-n-butoxy, 2,2-dimethyl-2(n-butoxy)ethoxy, 2-(n-butoxy)-1-methylethoxy, 2-isobutoxy-2-methylethoxy, 5-methoxy-n-pentyloxy, 4-methoxy-n-pentyloxy, 3-methoxy-n-pentyloxy, 5-ethoxy-n-pentyloxy, 4-ethoxy-n-pentyloxy, 3-ethoxy-n-pentyloxy, 5-(n-propoxy)-n-pentyloxy, 5-isopropoxy-n-pentyloxy, 6-methoxy-n-hexyloxy, 5-methoxy-n-hexyloxy, 4-methoxy-n-hexyloxy, 6-ethoxy-n-hexyloxy, 3-ethoxy-n-hexyloxy or 7-methoxy-n-heptyloxy; alkoxyalkyl with from 2 to 6 carbon atoms and of the form $R^6O—R^7—$, wherein $R^6$ represents alkyl and $R^7$ represents alkylene, each of $R^6$ and $R^7$ optionally being branched when it contains more than 3 carbon atoms, for example methoxymethyl, ethoxymethyl, n-propoxymethyl, isopropoxymethyl, n-butoxymethyl, n-pentyloxymethyl, 2-methoxyethyl, 2-ethoxyethyl, 2-(n-propoxy), 2-isopropoxyethyl, 2-(n-butoxy), 3-methoxy-n-propyl, 3-ethoxy-n-propoxy, 3-n-propoxy-n-propyl, 2-methoxy-2-methylethyl, 2-ethoxy-1-methylethyl, 2-(n-propoxy)-2-methylethyl, 2-isopropoxy-1-methylethyl, 4-methoxy-n-butyl, 4-ethoxy-n-butyl and 5-methoxy-n-pentyl.

Hydroxyalkoxy has from 2 to 6 carbon atoms, for example 2-hydroxyethoxy, 3-hydroxy-n-propoxy, 4-hydroxy-n-butoxy, 3-hydroxy-n-butoxy, 5-hydroxy-n-pentyloxy, 4-hydroxy-n-hexyloxy, 2-hydroxy-n-hexyloxy or 2-hydroxy-n-propoxy. The alkoxy of phenalkoxy is lower alkoxy, as in phenethoxy, but in particular benzyloxy. Substituted ureido is monosubstituted in the 3-position by linear or branched alkyl with from 1 to 6 carbon atoms, preferably with from 1 to 4 carbon atoms, by alkenyl with from 3 to 6 carbon atoms or by cycloalkyl with 5 or 6 ring carbon atoms, or disubstituted by lower alkyl and/or lower alkenyl. Examples of suitable ureido radicals are ureido, 3-methylureido, 3-ethylureido, 3-propylureido, 3-isopropylureido, 3-allylureido, 3-cyclopentylureido, 3-cyclohexylureido, 3,3-dimethylureido and 3,3-diethylureido. Halo includes iodo, but is preferably fluoro, chloro or bromo.

When $R^1$ and/or $R^2$ is acylamino, acyl is preferably carbocyclic aryl-substituted, carbocyclic aryl(lower)alkyl-substituted or alkyl-substituted carbonyl with up to 11 carbon atoms; it is thus derived from a carbocyclic aromatic, carbocyclic aromatic-aliphatic or aliphatic carboxylic acid. Examples of suitable acylamino radicals are acetamino, propionylamino, butyryl-amino, benzoylamino, α- and β-naphthoylamino and phenylacetylamino; acetamino and benzoylamino are preferred.

In addition to hydrogen (—H), $R^3$ optionally represents, in particular, alkyl with from 1 to 4 carbon atoms, for example methyl, ethyl, n-propyl, isopropyl, n-butyl or isobutyl.

The sole limitations on $R^1$ and $R^2$ are those of steric hindrance, which are readily determined by any skilled artisan with molecular models, and those of physiological acceptability, which are readily determined by any skilled pharmacologist from established routine standard tests. In such context compounds of formula I include those embodiments wherein the substituted or unsubstituted phenyl is appropriately regarded merely as mono(carbo)cyclic aryl, any substituent of which is limited only by pharmaceutical acceptability. In a somewhat more restricted sense those embodiments are included wherein each of $R^1$ and $R^2$ is hydrocarbyl having up to 8 carbon atoms, hydrocarbyloxy having up to 8 carbon atoms and hydrocarbonylamino having up to 12 carbon atoms. Regardless of the particular meaning of $R^1$ and $R^2$, either can be in any available position on the benzene nucleus which is not barred by steric hindrance.

Preferred pharmacologically-acceptable compounds are those which, in free-base form, are of formula I and wherein:
(a) n is 2,
(b) $R^3$ is methyl
(c) one of $R^1$ and $R^2$ (at least) is other than —H and is in the para-position of the phenyl nucleus, or
(d) one of $R^1$ and $R^2$ (at least) is hydroxyl, alkoxyalkoxy, alkoxy, alkoxyalkyl or hydroxyalkoxy.

Those of the preferred compounds which have two or more features depicted by (a), (b), (c) and (d) are particularly preferred. Those phenyl radicals which have no center of asymmetry are usually preferred for $R^1$ and/or $R^2$.

When compounds of formula I are not in free-base form, they are in the form of acid-addition salts.

Inorganic and organic acids are suitable for forming acid-addition salts with compounds of formula I. Examples of suitable acids are hydrogen chloride, hydrogen bromide, naphthalene-1,5-disulfonic acid, and phosphoric, nitric, sulfuric, oxalic, lactic, tartaric, acetic, salicyclic, benzoic, formic, propionic, pivalic, diethylacetic, malonic, succinic, pimelic, fumaric, maleic, malic, sulfamic, phenylpropionic, gluconic, ascorbic, isonicotinic, methanesulfonic, p-toluenesulfonic, citric or adipic acid. Pharmaceutically-acceptable acid-addition salts are preferred. Those acids which are suitable for preparing pharmaceutically-acceptable acid-addition salts are well known. The acid-addition salts are obtained in the customary manner by combining the components appropriately in a suitable diluent or dispersing agent.

For the manufacture of the compounds of formula I, a compound of the formula

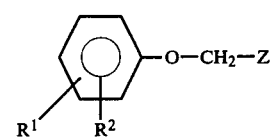

(V), wherein Z represents

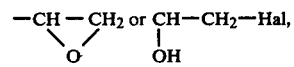

and

Hal denotes halo, in particular chloro or bromo, is reacted with a compound of the formula

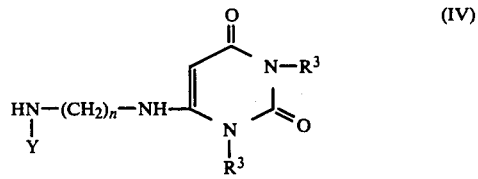

(IV)

wherein Y represents hydrogen (—H) or a radical which is subject to hydrogenolytic scission, such a radical, when present in the resulting compound, being subsequently split off by hydrogenolysis. The resulting compound is optionally reacted with an acid to obtain the corresponding acid-addition salt.

hydrogenolytic scission, the reaction of compounds of formulae IV and V initially yields compounds of formula Ia

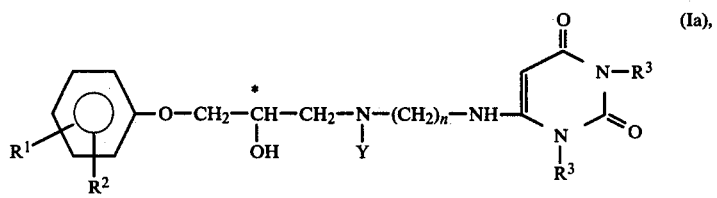

Instead of using a single compound of formula V, a mixture of a compound of formula II

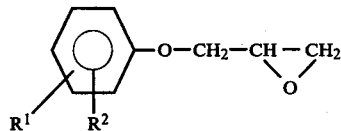

with a compound of the formula

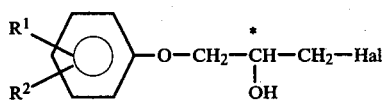

wherein Hal denotes halo, in particular chloro or bromo, is optionally employed. In such mixture the phenyl nucleus of both compounds are substituted in the same way.

The reaction of compounds of formulae IV and V is usually carried out in a suitable solvent or dispersing agent in which the reactants are dissolved or suspended. Examples of such solvents or dispersing agents are water; aromatic hydrocarbons, such as benzene, toluene or xylene; ketones, such as acetone or methyl ethyl ketone; halogenated hydrocarbons, such as chloroform, carbon tetrachloride, chlorobenzene or methylene chloride; ethers, such as tetrahydrofurane or dioxane; sulfoxides, such as dimethylsulfoxide; and tertiary acid amides, such as dimethylformamide or N-methylpyrrolidone. Polar solvents, such as alcohols, are particularly useful as solvents. Examples of suitable alcohols are methanol, ethanol, isopropanol and tert.-butanol. Alcohols with from 1 to 4 carbon atoms are preferred. The reaction is carried out at temperatures from 20° C. up to the reflux temperature of the solvent or dispersing agent used. The reaction frequently proceeds at temperatures of from 60° to 100° C. It is appropriate to employ the starting compound of formula IV in a molar excess of up to 10-fold and optionally even more and/or to add reactants of formulae II and III, in dissolved or suspended form, to dissolved or suspended reactant of formula IV. Hence, the molar ratio between compounds of formulae II and/or III and those of formula IV is, e.g., from 1:1 to 1:10 and, optionally, even less. When a compound of formula III is employed, the reaction is optionally conducted in the presence of an acid-binding agent, such as potassium carbonate, sodium carbonate or triethylamine, i.e. with such an acid-binding agent in the reaction medium. Without an acid-binding agent, hydrohalides of compounds of formula I are usually obtained when Y=hydrogen.

When Y in formula IV represents a radical, for example benzyl or carbobenzoxy, which is susceptible to hydrogenolytic scission, the reaction of compounds of formulae IV and V initially yields compounds of formula Ia wherein Y represents a radical which can be split off hydrogenolytically. When compounds of formula III are employed in the absence of an acid-binding agent, hydrohalides of compounds of formula Ia are obtained. Compounds of formula Ia or their hydrohalides are converted into compounds of formula I by hydrogenolytically splitting off the radical Y by conventional processes. For this, the compound of formula Ia or its hydrohalide is dissolved or suspended in a suitable solvent, such as an alkanol, e.g. ethanol; an ether, e.g. dioxane, or a hydrocarbon, e.g. toluene or xylene, and is then treated with hydrogen, appropriately in the presence of a suitable catalyst, such as palladium-on-charcoal, at a temperature within the range of from room temperature (20° C.) to the reflux temperature of the solvent used. After filtering off the catalyst, the compound of formula I is optionally isolated. The hydrogenolytic splitting off of radical Y is usually effected at room temperature (20° C.).

Starting compounds of formula IV are manufactured by reacting compounds of formula IV

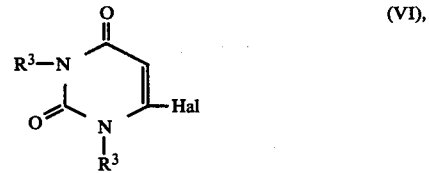

in which Hal represents halo, in particular chloro or bromo, with a compound of the formula

wherein X denotes a radical (which can be split off hydrolytically) or a protective group, or the radical Y (=hydrogen or a radical which can be split off hydrogenolytically). A radical which can be split off hydrolytically is, for example, acetyl or some other acyl, such as benzoyl, i.e., a radical which is derived (by splitting off —OH) from an aliphatic, aromatic or araliphatic carboxylic acid. As already mentioned, a radical which can be split off hydrogenolytically is, for example, benzyl or carbobenzoxy. The reaction of compounds of formula VI with compounds of formula VII is usually carried out in a suitable solvent or dispersing agent, i.e. one in which the reactants are dissolved or suspended, such as benzene, toluene, xylene, chloroform, methylene chloride, carbon tetrachloride, diethyl ether, dioxane, tetrahydrofurane, dimethylsulfoxide, acetone, methyl ethyl ketone, dimethylformamide or N-methylpyrrolidone. The molar ratio between compounds of formula VI and those of formula VII is optionally 1:1 to 1:10 or even less. The reaction is conducted at room temperature or is accelerated or brought to completion by applying heat, for example by heating to a temperature of from 80° to 110° C.

When X represents hydrogen in the reaction of a compound of formula VI with a compound of formula VII, the compound of formula VII is appropriately employed in excess, in some cases even as the solvent. When X represents a protective group which can be split off hydrolytically or hydrogenolytically and both the reactants are employed in equimolar amounts in the reaction of a compound of formula VI with a compound of formula VII, the reaction is appropriately carried out in the presence of an acid-binding agent, such as potassium carbonate, sodium carbonate or triethylamine.

When X represents a protective group in the reaction of a compound of formula VI with a compound of formula VII, a compound of the formula

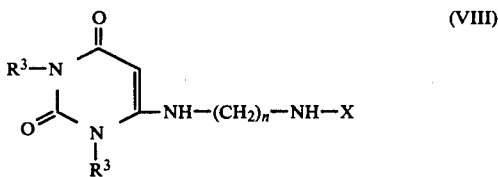

(VIII)

is first formed; from this compound a compound of formula IV, in which Y represents H, is obtained by conventionally cleaving the protective group X, for example by hydrolysis (when X represents an acyl radical) or by hydrogenolysis (when X represents a radical which can be split off hydrogenolytically).

For the manufacture of compounds of formula I, a pyrimidine of the formula

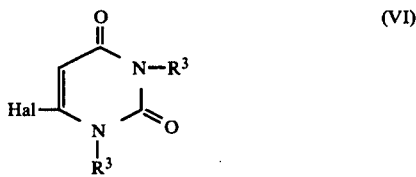

(VI)

is optionally reacted with a diamine of the formula

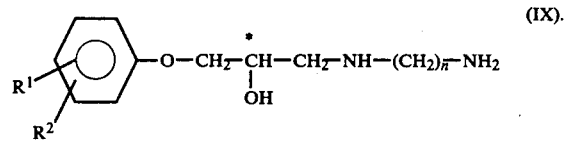

(IX).

The resulting compound is optionally reacted with an acid to obtain an acid-addition salt.

The reaction of a compound of formula VI with a compound of formula IX is usually carried out in a suitable solvent or dispersing agent, such as benzene, toluene, xylene, chloro-form, methylene chloride, carbon tetrachloride, chlorobenzene, dioxane, diethyl ether, tetrahydrofuran, water, dimethylsulfoxide, dimethylformamide or N-methylpyrrolidone, in which the reactants are dissolved or suspended.

The reaction is carried out at room temperature, or it is, optionally, accelerated or brought to completion by applying heat, for example by heating to a temperature between 80° and 120° C. The molar ratio between compounds of formula VI and those of formula IX is conveniently 1:1 to 1:10 and optionally even less. If equimolar amounts of the compounds of formulae VI and IX are employed, it is advisable to carry out the reaction in the presence of at least equimolar amounts of an acid-binding agent, such as potassium carbonate, sodium carbonate or triethylamine. Without acid-binding agents, the hydrohalides of compounds of formula I are usually obtained.

For the manufacture of starting diamines of formula IX, a compound of formula II, a compound of formula III, or a mixture of a compound of formula II with a compound of formula III (which is substituted in the henyl nucleus in the same way) is, e.g., reacted with a compound of formula VII (wherein X denotes hydrogen or a protective group, such as acetyl, which can be hydrolytically split off). This reaction is usually carried out in a suitable solvent or dispersing agent by dissolving or suspending the reactants therein. Examples of such solvents or dispersing agents are water; aromatic hydrocarbons, such as benzene, toluene and xylene; ketones, such as acetone and methyl ethyl ketone; halogenated hydrocarbons, such as chloroform, carbon tetrachloride, chlorobenzene and methylene chloride; ethers, such as tetrahydrofuran and dioxane; sulfoxides, such as dimethylsulfoxide; and tertiary acid amides, such as dimethylformamide and N-methylpyrrolidone. Polar solvents, such as alcohols, are used in particular as solvents. Examples of suitable alcohols are methanol, ethanol, isopropanol or tert.-butanol.

The reaction is carried out at temperatures from 20° C. up to the reflux temperature of the solvent or dispersing agent used. The reaction frequently proceeds at temperatures from 60° to 100° C. The starting compounds of formula VII are appropriately employed in an up to 10-fold and, optionally, even greater molar excess and/or the reactant of formula II and/or that of formula III, in the dissolved or suspended form, is added to the dissolved or suspended reactant of formula VII. Hence, the molar ratio between (a) the compound of formula II and/or that of formula III and (b) the compound of formula VII is, e.g., from 1:1 to 1:10 or, optionally, even less. When a compound of formula III is in the reaction mixture, the reaction is optionally effected in the presence of an acid-binding agent, such as potassium carbonate or sodium carbonate. Without acid-binding agents, the hydrohalides of compounds of formula IX are usually obtained.

When X represents a protective group in the reaction of a compound of formula II or of formula III with a compound of formula VII, a compound of the formula

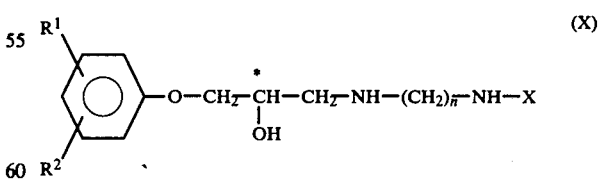

(X)

is formed. A compound of formula IX is obtained from the last-noted compound by splitting off the protective group X by customary methods, for example by hydrolysis when X represents an acyl radical.

The starting compounds of formula VI are either known or are easily manufactured in a known manner, for example from corresponding barbituric acid derivatives of formula XI, by reaction with inorganic acid chlorides, such as thionyl chloride; phosphorus halides, such as phosphorus tribromide or phosphorus pentachloride; or phosphorus oxyhalides, such as phosphorus oxychloride. Phosphorus oxychloride is preferably used for this reaction, and the reaction then proceeds as follows:

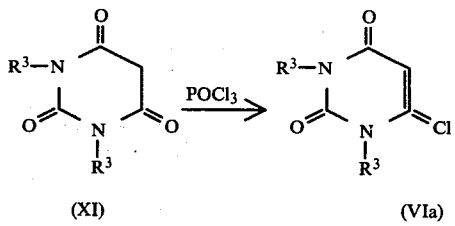

The compounds of formula II and of formula III are prepared conventionally, for example, by reacting corresponding phenols with epichlorohydrin.

An acid-addition salt is obtained by dissolving a free base of formula I in a suitable solvent, e.g. acetone, water or lower alkanol (ethanol, isopropanol), which contains the desired acid or to which the desired acid is subsequently added. The salt is obtained by filtration, precipitation with a non-solvent for the addition salt or by evaporation of the solvent.

An acid-addition salt, e.g. a hydrochloride, is converted into the corresponding free base by neutralization with aqueous sodium hydroxide or potassium hydroxide; the free base is then obtained by solvent extraction with a suitable water-immiscible solvent, such as chloroform, dichloromethane, diethyl ether, benzene, toluene or cyclohexane. The free base is alternatively obtained by neutralization of an acid-addition salt with sodium methylate in methanol and conventional isolation of the base according to known processes.

Optically-active forms of the alkylenediamines of formula I are obtained by resolving the corresponding racemic alkylenediamines of formula I using customary methods, for example by reacting the racemate of a compound of formula I with an optically-active-acid such, as tartaric acid, then subjecting the thus-obtained diastereomeric salt mixture to fractional crystallization from a suitable diluent or solvent, such as ethanol, and finally liberating the optically-active alkylenediamine from the salt with a base, e.g. NaOH or KOH. Optically-active compounds of formula I are also obtained by employing optically-active starting compounds III or IX. These optically-active starting compounds are obtained in a known manner from optically-inactive compounds III or IX, respectively, by resolving the racemate.

All starting materials for the synthesis of, e.g., compounds of formula I are known or are prepared in conventional manner according to known reactions from available compounds. References throughout the disclosure and claims to compounds which, in free-base form, are, e.g., of formula I include both the compounds of formula I and acid-addition salts thereof; the expression is thus generic to free bases and to acid-addition salts.

The compounds of formula I according to the invention and their acid-addition salts have valuable pharmaceutical properties. In particular they possess a highly-pronounced β-adrenolytic action, which is also cardioselective. The compounds possess a greater degree of specificity in the blocking of cardial β-receptors than of peripheral β-receptors, for example the β-receptors in the bronchial muscle. In addition, they possess powerful antiarrhythmic and hypotensive actions. They are therefore suitable, for example, for the treatment or prophylaxis of heart disorders and heart diseases, such as angina pectoris and cardia arrhythmias, and furthermore for the treatment of hypertension, with virtually no adverse side effects on the lungs of even sensitive patients.

Surprisingly, the pharmaceutical action of the compounds of formula I according to the invention is significantly superior to that of known compounds of a similar structure from U.S. Pat. No. 4,020,071.

The alkylenediamines according to the invention are administered to humans. They are administered individually, in mixtures with one another or in pharmaceutical formulations which contain, as active constituent, an active and effective dose of at least one alkylenediamine according to the invention or at least one acid-addition salt thereof, in addition to customary pharmaceutically-acceptable excipient and/or additive.

Examples of suitable excipients are water, vegetable oils, starch, gelatin, lactose, magnesium stearate, waxes or petroleum jelly. Examples of suitable additives are wetting agents, disintegrating agents and/or preservatives.

The pharmaceutical formulations are, for example, in the form of tablets, capsules, aqueous or oily solutions or suspensions, emulsions, injectable aqueous or oily solutions or suspensions, dispersible powders or aerosol mixtures.

Each of the pharmaceutically-acceptable compounds of this invention is, e.g., incorporated, for oral administration, in a tablet as the sole active ingredient. A typical tablet is constituted by from 1 to 3 percent binder, e.g. tragacanth; from 3 to 10 percent disintegrating agent, e.g. corn starch; from 2 to 10 percent lubricant, e.g. talcum; from 0.25 to 1.0 percent lubricant, e.g. magnesium stearate; an average dosage of active ingredient, e.g. a pharmacologically-acceptable compound of formula I; and q.s. 100 percent of filler, e.g. lactose; all percentages being by weight. Tablets are prepared according to standard tabletting techniques, which are well-known in the art, employing the necessary amounts of conventional granulating liquids, e.g. alcohol SD-30 and purified water. An exemplary tabletting formulation is:

| | |
|---|---|
| Compound of Example 1 | 70 parts |
| Tragacanth | 2. |
| Lactose | 20 |
| Corn Starch | 4.5 |
| Talcum | 3. |
| Magnesium Stearate | 0.5 |
| Alcohol SD-30 | q.s. |
| Purified Water | |

Replacing 5 mg of lactose with 5 mg of diazepam results in a tabletting formulation with a combination of active ingredients.

Unit dosage forms of pharmaceutical compositions for both oral and parenteral administration are conventionally prepared according to standard and well-established techniques. Such unit dosage forms contain, e.g., from about 1 to about 250, advantageously from about 3 to about 150 and, in particular, from about 5 to about 75, milligrams (mg) of pharmacologically-acceptable alkylenediamine of formula I or of pharmacologically-acceptable acid-addition salt thereof. In pharmaceutical preparations the alkylenediamine comprises from about 1 to about 95 percent by weight. The average daily dose is from about 0.1 to about 1.5 mg/kg of body weight and is administered either in a single dose or in from two to four divided doses, e.g., after meals and/or in the evening. Treatment is continued while the condition being treated persists, e.g. for several days. Doses for prophylaxis are ordinarily from one third to one half that for treatment, but are continued for a more-extended period of time.

The actual dose depends on the severity of the condition being treated and the general health, the age and the weight of the patient.

In addition to compounds of formula I, the pharmaceutical formulations optionally additionally contain one or more further and chemically and therapeutically-compatible pharmaceutically-active substances, for example tranquilizers, such as Luminal, meprobamate, chlorpromazines or benzodiazepine; sedatives, such as diazepam or chlordiazepoxide; vasodilators, such as glycerol trinitrate, pentaerythritol tetranitrate or carbochromene; diuretic agents, such as chlorothiazide; agents which improve the tonus of the heart, such as digitalis preparations; hypotensive agents, such as Rauwolfia alkaloids or Guanethidin; bronchodilators and sympathomimetic agents, such as isoprenaline, osciprenaline, adrenalin or ephedrine; α-adrenergic blocking agents, such as phentolamin; agents for stabilizing the cardiac membrane (antiarrhythmic agent), such as quinidine; and catecholamines, such as noradrenalin.

The following examples are merely illustrative embodiments and in no way limit the nature or scope of the invention.

EXAMPLE 1

7.4 grams (g) of N-[3-phenoxy-2-hydroxypropyl]ethylenediamine

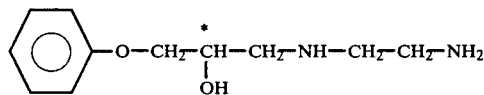

are dissolved in 80 milliliters (ml) of toluene. 5.8 g of potassium carbonate are added to the resulting solution, and 5 g of 1,3-dimethyl-6-chloropyrimidine-2,4-dione

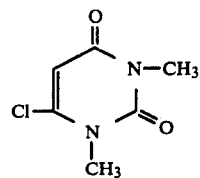

(dissolved in 50 ml of toluene) are then added dropwise at room temperature, while stirring, to the thus-obtained admixture. The mixture is then heated under reflux for 8 hours. After cooling the refluxed mixture to room temperature, it is filtered; the residue is extracted several times with water and filtered again. Thereafter, the residue is recrystallized from water. N-[3-phenoxy-2-hydroxypropyl]-N'-[1,3-dimethyl-2,4-dioxopyrimid-6-yl]ethylenediamine

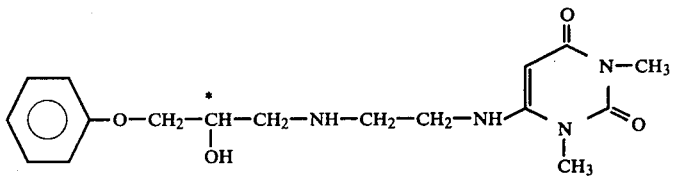

is thus obtained.

Melting point: 107° C. Analysis: ($C_{17}H_{24}N_4O_4$) Calculated: C 58.6; H 6.9; N 16.1; O 18.4. Found: 58.9; 7.1; 18.8; 18.3. Yield: 73% of theory.

The N-[3-phenoxy-2-hydroxypropyl]ethylenediamine used as the starting material is prepared, e.g., as follows: 100 g of ethylenediamine $H_2N$-$CH_2$-$CH_2$-$NH_2$ are dissolved in 200 ml of ethanol. A solution of 30 g of phenyl glycidyl ether.

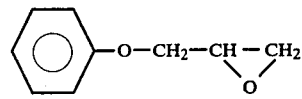

in 75 ml of ethanol is added to the thus-obtained solution, and the resulting mixture is heated under reflux for 20 hours. Ethanol is then distilled off in vacuo, and the produced residue is subsequently distilled in vacuo. N-[3-phenoxy-2-hydroxypropyl]ethylenediamine is thus obtained as an oil which distills at (boiling point) 170° C./0.2 millimeters (mm) and which becomes solid (melting point: 41° C.) after a short time.

The 1,3-dimethyl-6-chloropyrimidine-2,4-dione required as the starting material is prepared, e.g., by reacting 1,3-dimethylbarbituric acid with phosphorus oxychloride in known manner [for example, according to the method of W. Pfleiderer et al, Liebigs Annalen Chemie, 612, page 160 et seq. (1958)].

EXAMPLE 2

5.4 g of N-[3-{p-(2-[n-propoxy]ethoxy)phenoxy}-2-hydroxypropyl]ethylenediamine of the formula:

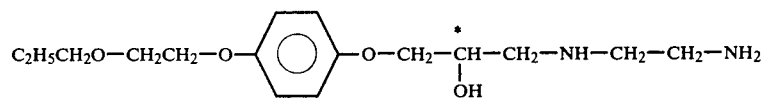

are dissolved in 50 ml of toluene, and 2.9 g of potassium carbonate are added to the thus-obtained solution. 2.5 g of 1,3-dimethyl-6-chloropyrimidine-2,4-dione

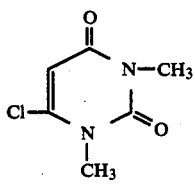

(dissolving in 25 ml of toluene) are added dropwise to the resulting mixture, while stirring. The mixture is then heated under reflux for 6 hours before cooling it to room temperature, filtering it and extracting the residue several times with water. The residue is then dissolved in 30 ml of 0.5 N hydrochloric acid. The produced hydrochloric-acid solution is buffered to pH 5 with potassium carbonate and then washed three times with ethyl acetate. The pH of the thus-washed aqueous solution is then adjusted with aqueous 2 N NaOH up to pH 9, and the alkaline aqueous solution is again extracted three times with ethyl acetate. The ethyl acetate extracts are dried and concentrated in vacuo. The residue is recrystallized from water.

N-[3-{p-(2-[n-Propoxy]ethoxy)phenoxy}-2-hydroxypropyl]-N'-[1,3-dimethyl-2,4-dioxopyrimid-6-yl]ethylenediamine of the formula

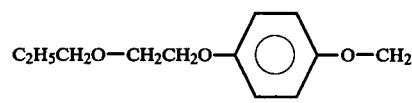

is thus obtained.

Melting point: 125° C. Analysis: ($C_{22}H_{34}N_4O_6$) Calculated: C 58.7; H 7.6; N 12.4; O 21.3. Found: C 58.9; H 7.8; N 12.2; O 21.1. Yield: 82% of theory.

The N-[3-(p-n-propoxyethoxyphenoxy)-2-hydroxypropyl]ethylenediamine used as the starting material is prepared, according to the procedure indicated in Example 1, from the corresponding phenyl glycidyl ether by reaction with ethylenediamine.

Replacing the starting N-[3-{p-(2-[n-propoxy]ethoxy)phenoxy}-2-hydroxypropyl]ethylenediamine with an equivalent of N-[3-(p-cyclohexyloxy)phenoxy-2-hydroxypropyl]ethylenediamine and otherwise proceeding according to the method of Example 2 results in obtaining a similar yield of the corresponding final product of formula I.

EXAMPLE 3

4.5 g of N-[3-(o-methylphenoxy)-2-hydroxypropyl]ethylenediamine

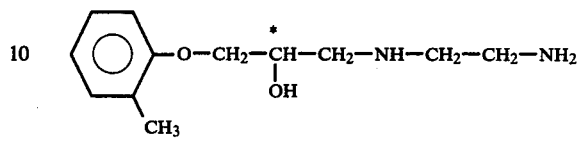

are dissolved in 100 ml of dioxane. 3 g of triethylamine are added to the thus-obtained solution. 3.5 g of 1,3-dimethyl-6-chloropyrimidine-2,4-dione

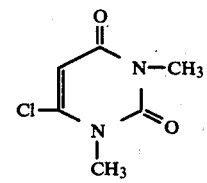

(dissolved in 100 ml of dioxane) are then added dropwise to the resulting admixture at room temperature, while stirring. The prepared mixture is then heated under reflux for 6 hours and filtered. The filtrate is concentrated in vacuo, and the residue is recrystallized from water. N-[3-(o-Methylphenoxy)-2-hydroxypropyl]-N'-[1,3-dimethyl-2,4-dioxopyrimid-6-yl]ethylenediamine

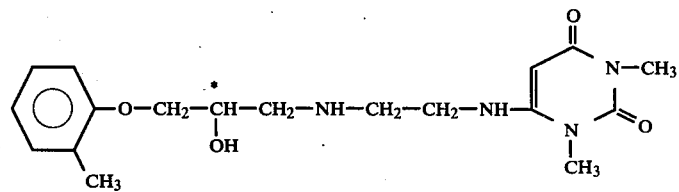

is thus obtained.

Melting point: 135° C. Analysis: ($C_{18}H_{26}N_4O_4$) Calculated: C 59.7; H 7.2; N 15.5; O 17.7. Found: C 59.6; H 7.3; N 15.3; O 18.0. Yield: 81% of theory.

EXAMPLE 4

3.1 g of N-[3-{p-(2-[n-propoxy]ethoxy)phenoxy}-2-hydroxypropyl]ethylenediamine of the formula

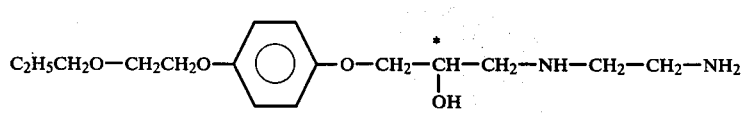

are dissolved in 30 ml of toluene, and 1.6 g of potassium carbonate are added to the thus-prepared solution. A solution of 2.3 g of 1,3-diisopropyl-6-chloropyrimidine-2,4-dione

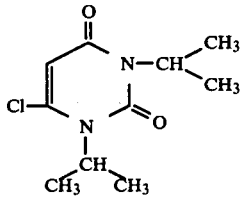

(in 30 ml of toluene) is added to the obtained mixture, which is then heated under reflux for 30 hours, cooled and filtered. The produced filtrate is concentrated in vacuo. The residue is dissolved in 40 ml of diethyl ether, and a small amount of insoluble material is filtered off. An etherial HCl solution is then added to the ether filtrate, whereupon a crystalline precipitate separates out. The precipitate is filtered off and recrystallized. N-[3-{p-(2-n-Propoxyethoxy)phenoxy}-2-hydroxypropyl]-N'-[1,3-diisopropyl-2,4-dioxopyrimid-6-yl]ethylenediamine of the following formula

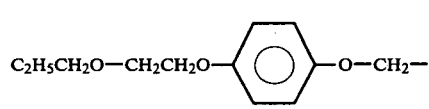

is thus obtained as the hydrochloride (melting point: 112° C.), from which the free base is obtained in the customary manner.

Analysis: ($C_{26}H_{42}N_4O_6$) Calculated: C 61.7; H 8.3; N 11.1; O 19.0. Found: C 61.5; H 8.5; N 10.9; O 18.7. Yield: 84% of theory.

Replacing the starting N-[3-{p-(2-[n-propoxy]ethoxy)phenoxy}-2-hydroxypropyl]ethylenediamine with an equivalent of N-[3-]p-(3-hydroxypropoxy)phenoxy}-2-hydroxypropyl]ethylenediamine and otherwise proceeding according to the method of Example 4 results in obtaining a similar yield of the corresponding final product of formula I.

EXAMPLE 5

4.5 g of 2-n-butoxyphenyl glycidyl ether

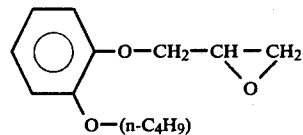

are heated under reflux together with 5.8 g of N-benzyl-N'-[1,3-dimethyl-2,4-dioxopyrimid-6-yl]ethylenediamine

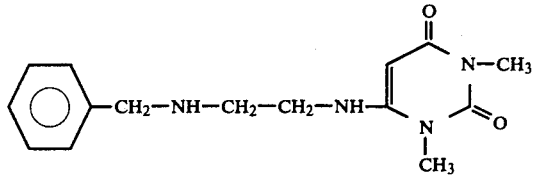

(in 150 ml of ethanol) for 2 hours. The resulting solution is then cooled and concentrated in vacuo. A resinous residue remains. This residue is dissolved in 150 ml of dioxane (without further purification) and then hydrogenated with $H_2$ in the presence of Pd/C at 20° C. for 10 hours. The catalyst is then filtered of; the filtrate is concentrated; and the residue is recrystallized once from toluene. N-[3-(o-Butoxyphenoxy)-2-hydroxypropyl]-N'-[1,3-dimethyl-2,4-dioxopyrimid-6-yl]ethylenediamine of the formula

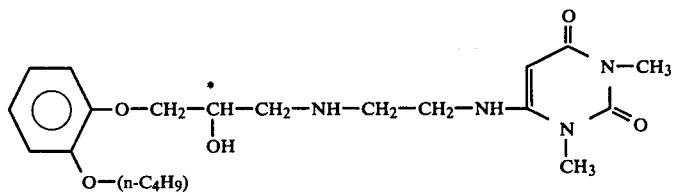

is thus obtained.

Melting point: 129° C. Analysis: ($C_{21}H_{32}N_4O_5$) Calculated: C 60.0; H 7.6; N 13.3. Found: C 59.8; H 7.7; N 13.1. Yield: 74% of theory.

The N-benzyl-N'-[1,3-dimethyl-2,4-dioxopyrimid-6-yl]ethylenediamine used as the starting material is obtained by reacting 1,3-dimethyl-6-chloropyrimidine-2,4-dione with N-benzylethylenediamine in boiling toluene, N-benzyl-N'-[1,3-dimethyl-2,4-dioxopyrimid-6-yl]ethylenediamine precipitating as the hydrochloride (melting point: 250° C., decomposition). The free base (melting point: 112° C.) is obtained from the hydrochloride with aqueous sodium carbonate solution.

The compounds mentioned in the following table are prepared according to the procedures of Examples 1 to 5:

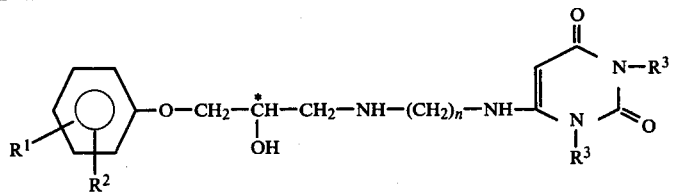

| Example No. | R¹ | R² | n | R³ | Melting Point |
|---|---|---|---|---|---|
| 6 | 2-OC$_2$H$_5$ | H | 2 | CH$_3$ | 112° C. |
| 7 | 4-OCH$_2$CH$_2$CH$_2$C$_2$H$_5$ | H | 2 | CH$_3$ | 131° C. |
| 8 | 4-OCH$_2$CH$_2$OCH$_2$C$_2$H$_5$ | H | 3 | CH$_3$ | 140° to 141° C. |
| 9 | 4-OCH$_2$CH$_2$CH$_2$C$_2$H$_5$ | H | 2 | —CH(CH$_3$)$_2$ | 98° C. (tartrate) |
| 10 | 4-OCH$_2$CH$_2$CH$_2$C$_2$H$_5$ | H | 3 | CH$_3$ | 143° C. |
| 11 | 4-OCH$_3$ | H | 2 | CH$_3$ | 130° to 131° C. |
| 12 | 4-OCH$_2$C$_2$H$_5$ | H | 2 | CH$_3$ | 138° to 139° C. |
| 13 | 4-OCH$_2$CH$_2$C$_2$H$_5$ | H | 2 | CH$_3$ | 126° to 127° C. |
| 14 | 4-OCH$_2$CH$_2$OH | H | 2 | CH$_3$ | 118° C. |
| 15 | 3-OCH$_3$ | H | 2 | CH$_3$ | 156° C. |
| 16 | 4-C$_2$H$_5$ | H | 2 | CH$_3$ | 119° C. |
| 17 | 2-OCH$_3$ | 4-CH$_2$CH=CH$_2$ | 2 | CH$_3$ | 175° C. (hydrochloride) |
| 18 | 2-Cl | H | 2 | CH$_3$ | 191° C. (hydrochloride) |
| 19 | 4-O—CH$_2$—C$_6$H$_5$ | H | 2 | CH$_3$ | 167° C. (naphthalene-disulfonate) |
| 20 | 4-OH | H | 2 | CH$_3$ | 227° C. |
| 21 | 2-Cl | 6-Cl | 2 | CH$_3$ | 215° C. (hydrochloride) |
| 22 | 2-OCH$_3$ | 3-OCH$_3$ | 2 | CH$_3$ | 146° C. |
| 23 | 3-CF$_3$ | H | 3 | C$_2$H$_5$ | 141° C. |
| 24 | 2-CH$_3$ | 4-CH$_3$ | 3 | n-C$_4$H$_9$ | 164° C. |
| 25 | 2-O—CH$_2$—CH=CH$_2$ | H | 3 | n-C$_3$H$_7$ | 133° C. |
| 26 | 2-cyclopentyl | H | 2 | C$_2$H$_5$ | 183° C. (hydrochloride) |
| 27 | 2-O—CH$_2$—C≡CH | H | 3 | CH$_3$ | 151° C. |
| 28 | 2-phenyl | 2 | 2 | i-C$_3$H$_7$ | 112° C. |
| 29 | 4-C(CH$_3$)$_3$ | H | 3 | C$_2$H$_5$ | 117° C. |
| 30 | 2-OCH$_3$ | 6-OCH$_3$ | 2 | CH$_3$ | 189° C. |
| 31 | 4-NH—CO—CH$_3$ | H | 3 | CH$_3$ | 139° C. |
| 32 | 2-CO—CH$_3$ | H | 3 | CH$_3$ | 146° C. |
| 33 | 4-CH$_2$—O—C$_2$H$_5$ | H | 2 | i-C$_3$H$_7$ | 162° C. |
| 34 | 4-NH—CO—NH-cyclohexyl | H | 3 | C$_2$H$_5$ | 191° C. |
| 35 | 4-CH$_2$O—CH$_3$ | H | 3 | CH$_3$ | 118° C. |
| 36 | 4-NH—CO—NH—C$_2$H$_5$ | H | 3 | CH$_3$ | 154° C. |
| 37 | 4-NH—CO—NH—CH$_2$—CH=CH$_2$ | H | 2 | n-C$_3$H$_7$ | 177° C. |
| 38 | 4-NH—CO—NH$_2$ | H | 3 | CH$_3$ | 182° C. |
| 39 | 4-NH—CO—N(morpholino) | H | 2 | CH$_3$ | 186° C. |
| 40 | 2-cyclopentenyl | H | 3 | n-C$_4$H$_9$ | 111° C. |

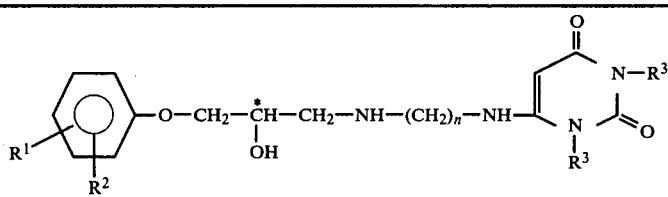

| Example No. | R¹ | R² | n | R³ | Melting Point |
|---|---|---|---|---|---|
| 41 | 2-C₆H₁₁ | H | 2 | i-C₃H₇ | 145° C. |
| 42 | 2-CH₃ | 4-Cl | 3 | CH₃ | 163° C. |
| 43 | 2-Cl | 4-CH(CH₃)₂ | 3 | CH₃ | 171° C. |
| 44 | 2-CH(CH₃)₂ | 4-Cl | 3 | C₂H₅ | 168° C. |
| 45 | 4-NO₂ | H | 3 | CH₃ | 122° C. |
| 46 | 2-CH₂—C≡CH | H | 3 | n-C₃H₇ | 147° C. |
| 47 | 4-CH₂—O—C₂H₅ | H | 2 | CH₃ | 166° C. |

The compounds of Examples 2, 7, 12, 13, 14, 15, 17, 19, 20 and 47 are preferred.

Pharmacological tests for activity towards $\beta_1$-receptors and $\beta_2$-receptors were carried out on mongrel dogs of both sexes under chloralose/urethane/morphine anaesthesia. The pressure in the left ventricle was recorded by means of a catheter tip manometer (micro-tip pressure transducer, MILLAR Instruments, Houston, Texas). The pressure signal was continuously differentiated by means of an analog computer and recorded (BRUSH Instruments, Cleveland, Ohio). The flow of blood through an arteria femoralis was measured and recorded by means of an electromagnetic flow meter (Messrs. STATHAM, Model M4000). Injection catheters were fastened to a peripheral vein and into a branch of the a. femoralis.

Isoproterenol was injected intravenously (0.5 gamma/kg) and intraarterially (0.05 gamma/kg). The effect of the isoproterenol on the dp/dt$_{max}$ in the case of intravenous administration was considered to be an expression of the stimulation of the $\beta_1$-receptors of the heart. The change in the flow of blood through the arteria femoralis in the case of intraarterial injection of isoproterenol was considered to be an expression of the stimulation of the peripheral $\beta_2$-receptors (D-DUNLOP and R. G. SHANKS, "Selective Blockade of Adrenoceptive beta-Receptors in the Heart", Br. J. Pharmac. Chemother., 32, 201 to 218, 1968). The percentage inhibition of the effects of isoproterenol with respect to the cumulative doses of the test substance was determined. The cumulative doses of the test substance which leads to 50% inhibition of the isoproterenol effects (=ED$_{50}$) was determined by means of a modified probit analysis. Substances which inhibit the isoproterenol effects on the dp/dt$_{max}$($\beta_1$) at a low dose and only decrease the change in the flow of blood through the a. femoralis at higher doses ($\beta_2$) preferentially act on the $\beta_1$-receptors of the heart. The ratio of the doses.

$$\frac{ED_{50}\,\beta_2}{ED_{50}\,\beta_1}$$

should be as high as possible. A number significantly >1 indicates a cardioselective action of the test substance.

The results obtained are listed in the table which follows:

| R¹ | ED$_{50}$ $\beta_1$ mg/kg intravenously | ED$_{50}$ $\beta_2$ mg/kg intraveneously | $\frac{ED_{50}\,\beta_2}{ED_{50}\,\beta_1}$ |
|---|---|---|---|
| 4-O—(n-C₄H₉) | 0.0096 | > 9.6 | > 1,000 |
| 4-OCH₃ | 0.0157 | 5.36 | 341 |
| 4-O—(n-C₃H₇) | 0.0061 | > 7.3 | > 1,000 |
| 4-OC₂H₄OH | 0.0291 | 8.83 | 303 |
| 4-OCH₂C₆H₅ | 0.0139 | 4.48 | 322 |

The invention and its advantages are apparent from the foregoing description. Various changes may be made in the compound structures and in the composition formulations without departing from the spirit or scope of the invention or sacrificing its material advantages. The presented processes, compounds, compositions and uses are merely illustrative of preferred embodiments of the invention.

What is claimed is:

1. Physiologically-active and pharmacologically-acceptable N-[3-{optionally-substituted phenoxy}-2-hydroxypropyl]-N'-[{unsubstituted or 1,3-di(lower)alkyl}-2,4-dioxopyrimid-6-yl]-α,ω-(ethylene or n-propylene)diamine wherein the optionally-substituted phenoxy is unsubstituted phenoxy or phenoxy substituted with at most two ring substituents which are independently selected from the group consisting of hydroxyl; halo; nitro; trifluoromethyl; hydrocarbyl having up to 8 carbon atoms; hydroocarbyloxy having up to 8 carbon atoms; alkanoyl having from 1 to 6 carbon atoms; alkoxyalkoxy having up to 8 carbon atoms; alkoxyalkyl having from 2 to 6 carbon atoms; hydroxyalkoxy having from 2 to 6 carbon atoms; hydrocarbylcarbonylamino having up to 12 carbon atoms; ureido; ureido monosubstituted in the 3-position by a substituent selected from the group consisting of alkyl with from 1 to 6 carbon atoms, alkenyl with from 3 to 6 carbon atoms and cycloalkyl with 5 or 6 ring carbon atoms; 3,3-disubstituted ureido, each substituent of which is, independently, lower alkyl or lower alkenyl; morpholino—CO—NH—; piperidino—CO—NH; and 1-pyrrolidinyl—CO—NH—.

2. A pharmacologically-acceptable compound which, in free-base form, is an ethylenediamine according to claim 1.

3. A pharmacologically-acceptable compound which, in free-base form, is an n-propylenediamine according to claim 1.

4. A pharmacologically-acceptable compound which, in free-base form, is a compound according to claim 1 wherein the 2,4-dioxopyrimid-6-yl is unsubstituted in each of the 1- and 3-positions.

5. A pharmacologically-acceptable compound which, in free-base form, is a compound according to claim 1 having 1,3-di(lower)alkyl-2,4-dioxopyrimid-6-yl in its molecular structure.

6. A pharmacologically-acceptable compound which, in free-base form, is a compound according to claim 1 wherein the optionally-substituted phenoxy is unsubstituted phenoxy.

7. A pharmacologically-acceptable compound which in free-base form, is a compound according to claim 1 and the optionally-substituted phenoxy is substituted phenoxy with at most two ring substituents which are independently selected from the group consisting of hydroxyl; halo; nitro; trifluoromethyl hydrocarbyl having up to 8 carbon atoms; hydrocarbyloxy having up to 8 carbon atoms; alkanoyl having from 1 to 6 carbon atoms; alkoxyalkoxy having up to 8 carbon atoms; alkoxyalkyl having from 2 to 6 carbon atoms; hydroxyalkoxy having from 2 to 6 carbon atoms; hydrocarbylcarbonylamino having up to 12 carbon atoms; ureido; ureido monosubstituted in the 3-position by a substituent selected from the group consisting of alkyl with from 1 to 6 carbon atoms, alkenyl with from 3 to 6 carbon atoms and cycloalkyl with 5 to 6 ring carbon atoms; 3,3-disubstituted ureido, such substituent of which is, independently, lower alkyl or lower alkenyl; morpholino—CO—NH—; piperidino—CO—NH—; and 1-pyrrolidinyl—CO—NH—.

8. A pharmacologically-acceptable compound, which in free-base form, is a compound according to claim 1 and the optionally-substituted phenoxy is phenoxy substituted by a substituent selected from the group consisting of hydroxyl, halo, nitro and trifluoromethyl.

9. A pharmacologically-acceptable compound which, in free-base form, is a compound according to claim 1 and the optionally-substituted phenoxy is phenoxy substituted by a substituent selected from the group consisting of hydrocarbyl having up to 8 carbon atoms, hydrocarbyloxy having up to 8 carbon atoms, alkenoyl having from 1 to 6 carbon atoms, alkoxyalkoxy having up to 8 carbon atoms, alkoxyalkyl having from 2 to 6 carbon atoms, hydroxyalkoxy having from 2 to 6 carbon atoms and hydrocarbylcarbonylamino having up to 12 carbon atoms.

10. A pharmacologically-acceptable compound which, in free-base form, is a compound according to claim 1 and the optionally-substituted phenoxy is phenoxy substituted by a substituent selected from the group consisting of ureido; ureido monosubstituted in the 3-position by a substituent selected from the group consisting of alkyl with from 1 to 6 carbon atoms, alkenyl with from 3 to 6 carbon atoms and cycloalkyl with 5 or 6 ring carbon atoms; and 3,3-disubstituted ureido, each substituent of which is, independently, lower alkyl or lower alkenyl.

11. A pharmacologically-acceptable compound which in free-base form, is a compound according to claim 1 and the optionally-substituted phenoxy is phenoxy substituted by morpholino—CO—NH—.

12. A pharmacologically-acceptable compound which, in free-base form, is a compound according to claim 1 and the optionally-substituted phenoxy is phenoxy substituted by piperidino—CO—NH—.

13. A pharmacologically-acceptable compound which, in free-base form, is a compound according to claim 1 and the optionally-substituted phenoxy is phenoxy substituted by 1-pyrrolidino—CO—NH—.

14. A pharmacologically-acceptable compound according to claim 7 and of the formula

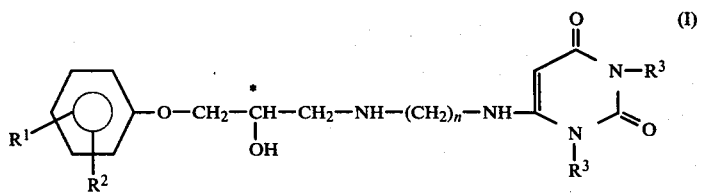

wherein
\* designates an asymmetric carbon atom;
each of $R^1$ and $R^2$ is, independently, a member selected from the group consisting of —H, hydroxyl, halo, nitro, trifluoromethyl, alkyl, alkenyl, alkinyl, cycloalkyl, cycloalkenyl, alkoxy, cycloalkoxy, alkenyloxy, alkinyloxy, phenalkoxy, alkanoyl, alkoxyalkoxy, alkoxyalkyl, hydroxyalkoxy, phenyl, carboxylic acid acylamino, optionally-substituted ureido and —NH—CO—R$^8$;

R$^3$ is —H or lower alkyl;

R$^8$ is morpholino, piperidino or 1-pyrrolidinyl; and n is 2 or 3.

15. A compound according to claim 14 wherein at least one of R$^1$ and R$^2$ is a member selected from the group consisting of fluoro, chloro, bromo, —H, hydroxyl, trifluoromethyl, nitro, phenyl, alkyl with from 1 to 8 carbon atoms, alkenyl with up to 6 carbon atoms, alkynyl with up to 6 carbon atoms, cycloalkyl with from 5 to 8 ring carbon atoms, cycloalkenyl with from 5 to 8 ring carbon atoms, alkoxy with 1 to 8 carbon atoms, cycloalkoxy with from 5 to 8 ring carbon atoms, alkenyloxy with up to 6 carbon atoms, alkynyloxy with up to 6 carbon atoms, phenethoxy, benzyloxy, alkanoyl with from 1 to 6 carbon atoms, alkoxyalkoxy with a total of up to 8 carbon atoms, alkoxyalkyl with from 2 to 6 carbon atoms, hydroxyalkoxy with from 2 to 6 carbon atoms, —NH—CO—R$^8$, carboxylic acid acylamino with up to 11 carbon atoms in the acyl radical, ureido, ureido which is monosubstituted in the 3-position by cycloalkyl with 5 or 6 ring carbon atoms and ureido which is monosubstituted or disubstituted in the 3-position by alkyl with from 1 to 6 carbon atoms and/or by alkenyl with from 3 to 6 carbon atoms.

16. A compound according to claim 14 wherein one of R$^1$ and R$^2$ is other than —H and in the para-position of the phenyl nucleus.

17. A compound according to claim 14 wherein R$^3$ is methyl.

18. A compound according to claim 14 wherein at least one of R$^1$ and R$^2$ is alkoxyalkoxy with a total of up to 8 carbon atoms.

19. A compound according to claim 14 wherein at least one of R$^1$ and R$^2$ is alkoxyalkyl with from 2 to 6 carbon atoms.

20. A compound according to claim 14 wherein at least one of R$^1$ and R$^2$ is hydroxyalkoxy with from 2 to 6 carbon atoms.

21. A compound according to claim 14 wherein at least one of R$^1$ and R$^2$ is alkoxy with from 1 to 8 carbon atoms.

22. A compound according to claim 14 wherein at least one of R$^1$ and R$^2$ is hydroxyl.

23. A member selected from the group consisting of the compound according to claim 2 which is N-[3-(p-methoxy)-phenoxy-2-hydroxypropyl]-N'-[1,3-dimethyl-2,4-dioxopyrimid-6-yl]ethylenediamine and a pharmacologically acceptable acid-addition salt thereof.

24. A member selected from the group consisting of the compound according to claim 2 which is N-[3-{p-(n-propyloxy)phenoxy}-2-hydroxypropyl]-N'-[1,3-dimethyl-2,4-dioxopyrimid-6-yl]ethylenediamine and a pharmacologically-acceptable acid-addition salt thereof.

25. A member selected from the group consisting of the compound according to claim 2 which is N-[3-{p-(n-butoxy)-phenoxy}-2-hydroxypropyl]-N'-[1,3-dimethyl-2,4-dioxopyrimid-6-yl]ethylenediamine and a pharmacologically-acceptable acid-addition salt thereof.

26. A member selected from the group consisting of the compound according to claim 2 which is N-[3-{p-(n-pentoxy)-phenoxy}-2-hydroxypropyl]-N'-[1,3-dimethyl-2,4-dioxopyrimid-6-yl]ethylenediamine and a pharmacologically-acceptable acid-addition salt thereof.

27. A member selected from the group consisting of the compound according to claim 2 which is N-[3-{p-(2-[n-propoxy]ethoxy)phenoxy}-2-hydroxypropyl]-N'-[1,3-dimethyl-2,4-dioxopyrimid-6-yl]ethylenediamine and a pharmacologically-acceptable acid-addition salt thereof.

28. A member selected from the group consisting of the compound according to claim 2 which is N-[3-{p-(2-hydroxyethoxy)phenoxy}-2-hydroxypropyl]-N'-[1,3-dimethyl-2,4-dioxopyrimid-6-yl]ethylenediamine and a pharmacologically-acceptable acid-addition salt thereof.

29. A member selected from the group consisting of the compound according to claim 2 which is N-[3-{2-methoxy-4-(n-propyl)phenoxy}-2-hydroxypropyl]-N'-[1,3-dimethyl-2,4-dioxopyrimid-6-yl]ethylenediamine and a pharmacologically-acceptable acid-addition salt thereof.

30. A member selected from the group consisting of the compound according to claim 2 which is N-[3-(p-benzyloxy)-phenoxy-2-hydroxypropyl]-N'-[1,3-dimethyl-2,4-dioxopyrimid-6-yl]ethylenediamine and a pharmacologically-acceptable acid-addition salt thereof.

31. A member selected from the group consisting of the compound according to claim 2 which is N-[3-(p-ethoxymethyl)-phenoxy-2-hydroxypropyl]-N'-[1,3-dimethyl-2,4-dioxopyrimid-6-yl]ethylenediamine and a pharmacologically-acceptable acid-addition salt thereof.

32. A member selected from the group consisting of the compound according to claim 2 which is N-[3-(p-hydroxyphenoxy-2-hydroxypropyl]-N'-[1,3-dimethyl-2,4-dioxopyrimid-6-yl]ethylenediamine and a pharmacologically-acceptable acid-addition salt thereof.

33. A pharmacologically-acceptable acid-addition salt of a compound according to claim 1.

34. A pharmacologically-acceptable compound which, in free-base form, is a diamine according to claim 1.

* * * * *

UNITED STATES PATENT AND TRADEMARK OFFICE
CERTIFICATE OF CORRECTION

PATENT NO. : 4,216,314

DATED : August 5, 1980

INVENTOR(S) : Thomas RAABE, Otto GRÄWINGER, Josef SCHOLTHOLT and Eckhard SCHRÄVEN It is certified that error appears in the above-identified patent and that said Letters Patent are hereby corrected as shown below:

Column 21, line 19, "hydroocarbyloxy" should read --hydrocarbyloxy--; line 65, "trifluoromethyl" should read --trifluoromethyl;--. Column 22, line 7, "to" should read --or--; line 8, "such" should read --each--; line 12, "compound," should read --compound--; line 13, "which" should read --which,--; line 24, "alkenoyl" should read --alkanoyl--; line 41, "which" should read --which,--.

Signed and Sealed this

Twenty-eighth Day of April 1981

[SEAL]

Attest:

RENE D. TEGTMEYER

Attesting Officer     Acting Commissioner of Patents and Trademarks